United States Patent

Sung

[11] 4,266,944
[45] May 12, 1981

[54] FUEL COMPOSITIONS CONTAINING ACYL GLYCINE OXAZOLINES

[75] Inventor: Rodney L. Sung, Fishkill, N.Y.

[73] Assignee: Texaco Inc., White Plains, N.Y.

[21] Appl. No.: 104,520

[22] Filed: Dec. 17, 1979

[51] Int. Cl.³ .......................... C10L 1/18; C10L 1/22
[52] U.S. Cl. .................................... 44/63; 252/392; 252/394; 548/233
[58] Field of Search ................... 44/63; 548/233; 252/392, 394, 57.5 A

[56] References Cited

U.S. PATENT DOCUMENTS

| | | | |
|---|---|---|---|
| 4,035,309 | 7/1977 | Brois | 252/51.5 A |
| 4,049,564 | 9/1977 | Ryer et al. | 252/51.5 A |
| 4,150,143 | 4/1979 | Neville et al. | 548/233 |
| 4,153,566 | 5/1979 | Ryer et al. | 252/51.5 A |

Primary Examiner—Winston A. Douglas
Assistant Examiner—J. V. Howard
Attorney, Agent, or Firm—Carl G. Ries; Robert A. Kulason; Henry W. Archer

[57] ABSTRACT

Described are acyl glycine oxazolines of the formula:

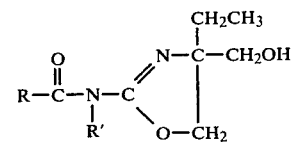

where R is lauryl, $C_{11}H_{23}$, oleyl or stearyl; and R' is hydrogen or lower alkyl. Also disclosed are motor fuel compositions in the gasoline boiling range containing a corrosion-inhibiting and detergent amount of the above compounds.

4 Claims, No Drawings

FUEL COMPOSITIONS CONTAINING ACYL GLYCINE OXAZOLINES

BACKGROUND OF THE INVENTION

1. Field of the Invention

This invention relates to hydrocarbon fuels and more particularly to fuels comprising a mixture of hydrocarbons in the gasoline boiling range and acyl glycine oxazolines acting as detergents therein.

As is well known hydrocarbon fuels have a tendency to form polymeric materials (variously called "gum" or "sludge" or "varnish") in various parts of fuel systems. These resin-like deposits tend to form in the fuel supply lines, fuel filter, carburetor, fuel control injectors, intake manifold and valve stems. Such deposits are objectionable not only because of their effect on mechanical performance but also because they decrease the breathing efficiency in engines of the spark ignition type.

Although each type of fuel is composed essentially of hydrocarbons their stability characteristics differ considerably. Thus typical automotive fuels contain straight and branched chains compounds while aircraft fuels contain a smaller proportion of olefins. Currently, certain types of fuels contain increased amounts of cracked stocks resulting in a higher olefin content and an increased susceptibility to the formation of gum.

For obvious reason, it is advantageous to use an additive which provides detergency property to the fuel.

2. Description of Prior Disclosures

Coassigned U.S. Pat. No. 3,773,479 describes a motor fuel composition comprising a mixture of hydrocarbons in the gasoline boiling range containing a minor amount of a substituted asparagine having the formula:

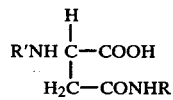

in which R and R' each represent a secondary or tertiary alkyl or alkylene radical having from about seven to about 20 carbon atoms. Coassigned U.S. Pat. No. 4,052,322 describes lubricating greases corrosion-inhibited by N-acyl sarcosines and sodium nitrite. Related subject matter is disclosed also in an article by Pine and Spivack in the publication "Corrosion," vol. 13, N.92 (1957) and in German Pat. No. 1,094,038.

SUMMARY OF THE INVENTION

The compounds of the invention are defined by the following structure:

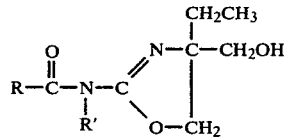

Where R is lauryl, $C_{11}H_{23}$, oleyl or stearyl; R' is hydrogen or (lower) alkyl. Preferably R and R' taken together contain from 13 to 21 carbon atoms.

Preferably, both the R and R' radicals are straight chain, however they also can be branched and may be substituted with one or more non-interfering substituents such as halogen, cyano, trifluoromethyl, nitro or alkoxy.

The invention also provides a motor fuel composition comprising a mixture of hydrocarbons in the gasoline boiling range containing a minor detergent and corrosion inhibiting amount of at least one of the above compounds; preferably, this amount ranges from 20 to 200 parts per thousand barrels of fuel.

The compounds of the invention preferably are synthesized by reacting a 2-amino-2-(lower) alkyl-1,3-propanediol with an N-acyl sarcosine in an inert solvent preferably xylene, refluxing the reaction mixture for about 8 hours to azeotrope the xylene and the water of reaction; filtering and stripping the filtrate under vacuum to isolate the product.

N-acyl sarcosines suitable as reactants include lauroyl sarcosine, cocoyl sarcosine, oleoyl sarcosine, stearoyl sarcosine and other fatty sarcosines containing from 8 to 22 carbon atoms. The preferred propanediol is 2-amino-2-ethyl-1,3-propanediol.

N-acyl sarcosines also known as "sarkosyls" previously suggested as corrosion inhibitors for fuels were found to be completely extracted into caustic water bottoms so that the fuels lost their corrosion inhibiting properties. Unexpectedly, it was found in accordance with this invention that the oxazolines of these compounds were completely unextractable by acidic or basic water bottoms.

Other compounds where R and R' are as stated above are similarly prepared and found to have the same utility.

The subject compounds can be incorporated in amounts ranging from about 20 to 200 parts per thousand barrels (PTB) in any gasoline suitable for a spark-ignited internal combustion engine. In general, the base fuel will consist of a mixture of hydrocarbons in the gasoline boiling range, i.e., boiling from about 75° to 450° F. The hydrocarbon components can consist of paraffinic, naphthenic, aromatic and olefinic hydrocarbons. This gasoline can be obtained naturally or it can be produced by thermal or catalytic cracking and/or reforming of petroleum hydrocarbons. The base fuel will generally have a Research Octane Number about 85 and up to about 102 with the preferred range being from about 90 to 100.

The present additives were tested in a carburetor detergency test.

This test is run on a Chevrolet V-8 engine mounted on a test stand using a modified four-barrel carburetor. The two secondary barrels of the carburetor are sealed and the feed to each of the primary barrels arranged so that separate fuels can be run in each barrel simultaneously. The primary carburetor barrels are also modified so that they have removable aluminum inserts in the throttle plate area in order that deposits formed on the inserts in this area can be conveniently weighed.

In the procedure designed to determine the effectiveness of an additive fuel to remove preformed deposits in the carburetor, the engine is run for a period of time, usually 24 to 48 hours, using the base fuel as the feed to both barrels with engine blow-by circulated to the air inlet of the carburetor. The weight of the deposits on both sleeves is determined and recorded. The engine is then recycled for 24 additional hours with a reference fuel being fed to one barrel, additive fuel to the other, and no blow-by to the carburetor air inlet. The reference fuel contains 15 PTB of a carburetor detergent. The inserts are then removed from the carburetor and weighed to determine the difference between the performance of the additive and non-additive fuels in removing the performed deposits. After the aluminum inserts are cleaned, they are replaced in the carburetor and the process repeated with the fuels reversed in the carburetor to minimize differences in fuel distribution and barrel construction. The effectiveness of the additive fuel is expressed as the difference Δ between deposit removed by the additive fuel and the deposit removed by base fuel. When Δ is positive, the additive fuel has removed more deposit than the reference fuel.

The motor fuel used as a standard for comparison purposes in this test is a commercial high octane premium gasoline containing a highly effective carburetor detergent. The fuel composition representative of the invention consisted of Base Fuel A described above containing the indicated amounts of the additive of the invention. The results of this test are reported as the difference in carburetor deposits removed by the additive containing gasoline of the invention in comparison to the commmercial premium detergent gasoline.

The results of the Chevrolet Carburetor Detergency Test are set forth in the following Table I.

The invention is further illustrated in non-limiting fashion by the following examples:

EXAMPLE I

Synthesis of Oxazoline of Sarkosyl 0

A mixture of 0.7 mole of oleyl sarcosine and 0.7 mole of 2 amino-2-ethyl 1,3 propanediol in 600 parts of xylene was refluxed & water of reaction was azeotroped over. After 8 hours of reflux, the reaction mixture was cooled and filtered, then stripped under vacuum. The residue was analyzed by I.R. and elemental analysis.

EXAMPLE II

A mixture of 0.7 mole of lauroyl sarcosine and 0.7 mole of 2-amino-2-ethyl, 1,3 propanediol in 600 ml. of xylene was refluxed and water of reaction was azeotroped over. At the end of 8 hours, the reaction was stripped, filtered, and stripped under vacuum. The residue was analyzed by I.R. and elemental analysis.

From the data of Table I it is seen that the present compounds are effective detergents for gasoline.

Furthermore, the data of Table I shows that in the case of runs 3 and 1 the present additives are equivalent to an experimental additive. Thus, in the case of runs 4 and 2, the data show that at 100 PTB one of the present additives is equivalent to 1035 PTB of a widely used commercial additive and is over 10 times more effective on a weight to weight basis.

The additives of the invention also have anti-corrosion properties as shown by their performance in the National Association of Corrosion Engineers (NACE) Rusting Test. In this test a determination is made of the ability of the gasoline to inhibit the rusting of ferrous parts when water becomes mixed with gasoline. Briefly stated, the test is carried out by stirring a mixture 300 ml of the test gasoline and 30 ml of water at 37.8° C. with a polished steel specimen completely immersed therein for a test period of 3½ hours. The percentage of the specimen that has rusted is determined by comparison with photographic standards. Further details of the procedure appear in NACE Standard TM-01-72 and ASTM D6651 1P-135 (Procedure A).

Table II below shows the results of this test for a representative compound of the invention at different concentrations in pounds per 1000 barrels (PTB) in and against an unleaded base fuel.

The data of Table II show that as little as 5 PTB of the additive substantially eliminates rusting.

TABLE II

| NACE RUST RATING of oxazoline of Sarkosyl 0 | |
|---|---|
| Concentration | Rust Rating |
| 10 PTB | Trace to 1% |
| 10 PTB | " |
| 5 PTB | " |
| 5 PTB | " |
| Unleaded base fuel | 50 to 100% |
| " | 50 to 100% |

The fuels of the invention may contain any additive conventionally employed in gasoline. Tetraalkyl lead, antiknock additives, dyes, corrosion inhibitors, antioxidants and the like can be beneficially employed without materially affecting the additive of the invention.

TABLE I

| | | CARBURETOR DETERGENCY TEST | | |
|---|---|---|---|---|
| | | % Deposit Removed | | |
| Run No. | Additive in S.C. + 3g./gal. of | Additive Fuel | Reference Fuel (1) | Δ |
| 1 | 20 PTB additive containing 60% of 2-polyisobutenyl lactono,-aminoethylimidazoline and 40% of polyisobutene | 48 | 26 | +22 vs. (a) |
| 2 | 0.20 (v) a blend of 3.00% solvent neutral oil oxidate, 37% of polypropene polymer, 57% of carrier oil and 15 PTB of the reaction product of maleic anhydride and Armeen L15 in solvent neutral oil and a carrier oil | 41 | +10 (b) | +51 vs. A |
| 3 | 20 PTB Oxazoline of Sarkosyl 0 | 68 | 67 | +1 vs. C |
| 4 | 100 PTB Oxazoline of Sarkosyl 0 | 83 | 89 | −6 vs. B |

(1) Reference Fuel A = Base Fuel B = contains 1035 PTB of a commercial additive package containing: N-butyl alcohol 15%, aromatic distillates 34%, polyisobutylenes 4%, polyisobutylenamines 9%.
(a) Fuel contains 15 PTB of the reaction product of maleic anhydride and Armeen L15 in solvent neutral oil oxidate and a carrier oil.
(b) + denotes deposit build-up.

What is claimed is:

1. A corrosion-inhibiting and detergent compound of the formula:

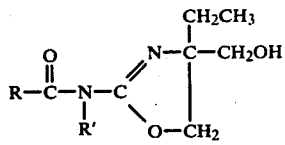

in which R represents lauryl, $C_{11}H_{23}$, oleyl or stearyl; and R' is hydrogen or lower alkyl.

2. The compound of claim 1, wherein R and R' taken together contain from 13 to 21 carbon atoms.

3. A motor fuel composition comprising a mixture of hydrocarbons in the gasoline boiling range containing a corrosion-inhibiting and detergent amount of at least one compound as defined in claim 1.

4. The composition of claim 3, wherein said compound is present in an amount ranging from about 20 to 2000 parts per thousand barrels of gasoline.

* * * * *